Figure 1:
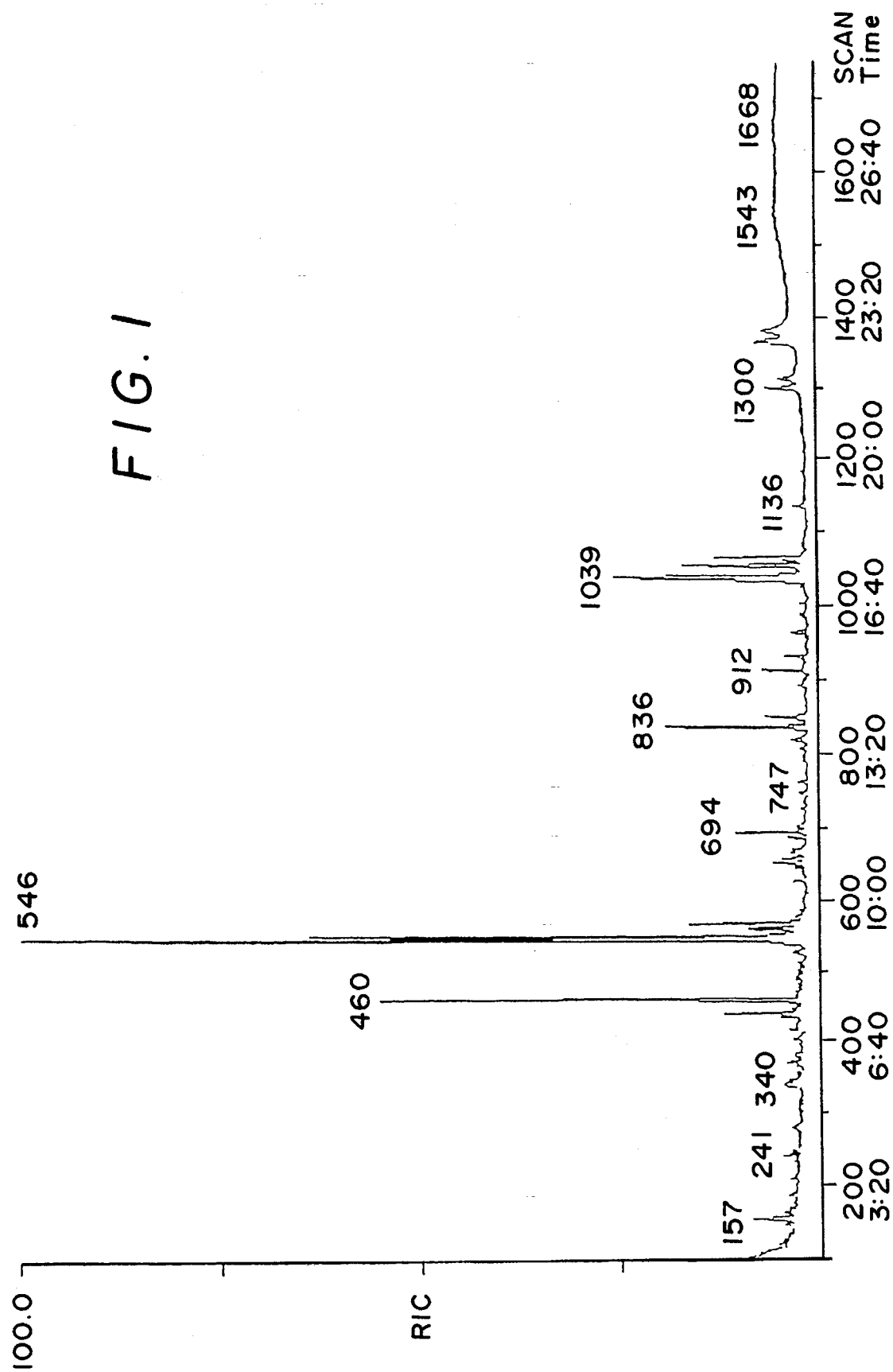

United States Patent [19]
Bombardelli

[11] Patent Number: 5,547,673
[45] Date of Patent: Aug. 20, 1996

[54] EXTRACTS OF CUCURBITA SP., PROCESS FOR THEIR PREPARATION AND THEIR USE IN MEDICAMENTS AND IN COSMETICS

[75] Inventor: Ezio Bombardelli, Milan, Italy

[73] Assignee: Indena S.p.A., Milan, Italy

[21] Appl. No.: 162,764

[22] Filed: Dec. 8, 1993

[30] Foreign Application Priority Data

Dec. 9, 1992 [DE] Germany .................... 42 41 487.3

[51] Int. Cl.$^6$ .................................................. A61K 35/78
[52] U.S. Cl. .................. 424/195.1; 514/783; 514/844; 514/859; 554/175; 800/DIG. 18
[58] Field of Search .................. 424/195.1; 514/859, 514/864; 800/DIG. 18, DIG. 19, DIG. 20, DIG. 21; 554/175

[56] References Cited

U.S. PATENT DOCUMENTS

| | | | |
|---|---|---|---|
| 4,255,418 | 3/1981 | Bailey | 424/145 |
| 4,421,746 | 12/1983 | Kojima et al. | 424/195.1 |
| 4,495,207 | 1/1985 | Christianson et al. | 426/312 |
| 4,692,280 | 9/1987 | Spinelli et al. | 260/420 |
| 4,820,537 | 4/1989 | Katz | 426/481 |
| 4,996,317 | 2/1991 | O'Brien et al. | 544/274 |
| 5,104,587 | 4/1992 | Besserman et al. | 554/175 |
| 5,124,313 | 6/1992 | Schaeffer et al. | 514/2 |

FOREIGN PATENT DOCUMENTS

| | | |
|---|---|---|
| 2522500 | 9/1983 | France . |
| WO92/13086 | 8/1992 | WIPO . |
| WO92/15563 | 9/1992 | WIPO . |

OTHER PUBLICATIONS

Seifen, Ole, Fette, Wachse, vol. 116, No. 16, Oct. 16, 1990, Augsburg DE, pp. 655–658, Michael Bork "Die Hochdruckextractio Mit CO2 Zur Gewinnung Naturlicher Extrakte".
Quirkin, K. W. et al.: "Supercritical carbon dioxide extraction of natural products for cosmetics and perfumery," Seifen, Ole, Fette, Wachse, 1991, 117(16), pp. 638–641.
Quisumbling (*Medicinal Plants of the Phillipines*, p. 930, (1951).

Primary Examiner—John Kight
Assistant Examiner—Howard C. Lee
Attorney, Agent, or Firm—Burns, Doane, Swecker & Mathis, L.L.P.

[57] ABSTRACT

A process for the preparation of novel extracts of *Cucurbita pepo* and cultivars thereof, the extracts obtainable thereby and their use in pharmacy and cosmetics are described. The said process comprises the following stages:

a) the milling of the Cucurbita seeds, where appropriate b) the extraction of the milled Cucurbita seeds with supercritical carbon dioxide at a temperature from 34° to 50° C. and under a pressure between 110 and 150 bar to remove unwanted products, c) the extraction of the active substances from the milled Cucurbita seeds with carbon dioxide under supercritical conditions or with organic solvents and d) the purification of the resulting extract by fractional countercurrent extraction with carbon dioxide under supercritical conditions. These extracts are used for the treatment of benign prostate hypertrophy and related clinical manifestations. The extracts are employed in cosmetics for the treatment of juvenile acne and as antiseborrhoea agents.

16 Claims, 4 Drawing Sheets

EXTRACTS OF CUCURBITA SP., PROCESS FOR THEIR PREPARATION AND THEIR USE IN MEDICAMENTS AND IN COSMETICS

DESCRIPTION

The present invention relates to the preparation of extracts from *Cucurbita pepo* seeds (such as *Cucurbita maxima, Cucurbita moscata, Cucurbita citrullina* and other species), to the extracts obtained and to their use in pharmaceuticals and cosmetics as specified in the patent claims.

The preparation process comprises the use of a combination of selective solvents in order to concentrate the active substances and to remove unwanted and toxic components, especially allergenic substances.

Additionally, the following documents have become known to the Applicant:

LIST, Heinz: "Technologie pflanzlicher Arzneizubereitungen." Wissenschaftliche Verlagsgesellschaft mbH Stuttgart 1984, pages 89–91, 116–117, 159–161, 171–173.

It describes extraction systems among which the extraction by supercritical gas.

VOGEL, P.: "Untersuchungen über Kürbiskernöl." In: Fette, Seifen, Anstrichmittel, Vol. 80, No. 8, 1978, pages 315–317, especially page 315, second column, last but one paragraph.

It describes the composition of Pumpkin seed oil.

N.N.: "Hochdruck-Extraktion von Naturstoffen mit $CO_2$." In: Seifen, Öle, Fette, Wachse, Vol. 112, No. 7, 1986, pages 218–220.

It describes the extraction of natural products, oils and natural fats with supercritical $CO_2$.

BORK, Michael: "Die Hochdruckextraktion mit $CO_2$ zur Gewinnung natürlicher Extrakte." In: Seifen, Öle, Fette, Wachse, Vol. 116, No. 16, 1990, pages 655–658.

It describes the use of supercritical $CO_2$ extraction for the preparation of natural products.

WILP, Ch.; EGGERS, R.: "Hochdruckextraktion mit mehrstufiger fraktionierender Separation zur schonenden Gewinnung von Keimöen mit hochverdichtetem Kohlendioxid." In: Fat Sci. Technol., Vol. 93, No. 9, pages 348–354.

It describes the $CO_2$ supercritical extraction of Corn germs. Rote Liste 1992, Nr. 81122.

It reports the composition of the proprietary medicinal product Prosta Fink containing also powdered seeds and oil of Cucurbita.

FR 26 73 375.

It claims the use of cucurbitine, pure or contained in Cucurbita extracts, in the cosmetic and pharmaceutical field as anti-allergic.

LIST, SCHMIDT: Technologie pflanzlicher Arzneizubereitungen, wbg Stuttgart, 1984, Seiten 161 bis 170.

It describes in detail the theory of the extraction with supercritical gas.

EP 0 129 739 B1.

It claims procedure and equipment for the obtention of fats and oils from plants with supercritical gas.

According to the state of the art (Cucurbita-Species, Portrait einer Arzneipflanze (Cucurbita species, portrait of a medicinal plant), Zeitschrift für Phytotherapie, 7 19–23, 1986), seeds of the species of Cucurbita are used as such or in the form of extracts for the treatment of dysuria associated with benign prostate hypertrophy. Although the health authorities in various countries have approved the use of Cucurbita products on the basis of the empirical applications, the efficacy of these products has not to date been demonstrated scientifically, and there are some uncertainties concerning the therapeutic value of the known extracts hitherto obtainable from the seeds of these plants.

Pharmacological and clinical data referring thereto are rather heterogeneous because to a great extent they were obtained in uncontrolled studies using products of uncertain origin in respect of the selected botanical species. Concerning the chemical composition, the seeds of Cucurbita pepo and cultivars derived therefrom contain fatty substances in a proportion in the range from 35 to 45%, normally 42%, in the form of an undefined oil which can be used as such for certain therapeutic applications, sterols in free and glucosidic form (Kneipp-Physiotherapie 5, 2–7, 1985) and a considerable amount of therapeutically important oligoelements such as selenium and zinc (Dtsch. Lebensm. Rundsch., 78, 39, 1982).

The pharmacological screening of the extracts from Cucurbita pepo carried out by the applicant reveals that the sterol fraction with its free and glycosidic components represents, together with the free fatty acids present in the extracts, one of the components active against prostatic disorders (cf. the mechanism of action thereof described hereinafter). Glycerides of fatty acids (diglycerides and monoglycerides), long-chain alcohols and procarotenoids purified by removal of worthless and interfering substances contribute to modulating the effect of the free sterols and their glucosides. The novel extracts prepared according to the invention have an activity which is a multiple of that of products prepared by conventional processes (solvent extraction, pressing out etc.).

The process according to the invention comprises a first stage (a), namely the milling of the Cucurbita pepo seeds. This stage (a) preferably takes place by intensive milling of the Cucurbita seeds at temperatures between −10° and +10° C., preferably between −7° and +2° C. and, in particular, at −5° C., under an inert gas atmosphere (preferably carbon dioxide atmosphere). This preferably starts from intact and hulled seeds. The particle size of the Cucurbita seeds milled in this way is expediently between 0.1 and 1 mm, preferably between 0.3 and 0.5 mm. If desired, the seeds are dried before milling. This drying of the seeds is preferably carried out in a drier with forced aeration at a temperature between 30° and 60° C., preferably between 35° and 55° C. The water content after drying should preferably be less than 10%, particularly preferably about 5%.

The process according to the invention comprises, where appropriate, a second stage (b), namely a preextraction with supercritical carbon dioxide to remove unwanted constituents and to concentrate the active substances. For this purpose, the material milled in stage (a) is extracted with supercritical carbon dioxide at a temperature from 34° to 50° C., preferably between 35° and 45° C., and under a pressure between 110 and 150 bar, preferably between 115 and 130 bar. An extraction of this type is able to remove unwanted products of low molecular weight. The extracts obtained under the stated conditions (34° to 50° C. and 110 to 150 bar), which account for about 22 to 33% (25%) of the weight of the seeds, are normally discarded.

This preextraction (b), which takes place where appropriate, is followed in the next stage by the actual extraction (c) of the active substances, and this can take place in a variety of ways. In a first variant, this extraction is carried out with supercritical carbon dioxide under a pressure between 250 and 330 bar, preferably between 270 and 310 bar, and at a temperature between 34 and 65° C., preferably between 40° and 50° C. The extraction is normally complete after a period of 2 to 6 hours, preferably of 3 to 5 hours. The flow rate depends on the extraction apparatus and is preferably between 7 and 12 kg per kg of plant material.

The plant material which has been subjected to stage (a) and, where appropriate, also stage (b) is, in a second variant of stage (c) (when extraction (c) is not to be carried out with supercritical carbon dioxide), exhaustively extracted with an organic solvent such as chlorinated aliphatic solvents such as chloroform, methylene chloride, dichloroethane or with acetone or with aliphatic alcohols such as methanol, ethanol etc., preferably with methylene chloride. The most suitable solvent for this is methylene chloride. The extraction is preferably carried out at temperatures between 25° C. and the boiling point of the solvent. The extraction of the plant material with these chlorinated aliphatic solvents, acetone or aliphatic alcohols preferably takes place using a total of 16 volumes of solvent per kg of plant material. 4 extractions each lasting 3 hours are preferably carried out.

The extract obtained after stage (c) can, especially when the extract has been obtained using one of the abovementioned chlorinated aliphatic solvents, acetone or aliphatic alcohols, be subjected to a treatment with an adsorbent such as active charcoal or diatomaceous earth.

The extracts obtained in extraction (c) are, in the next stage (d), subjected to countercurrent extraction with $CO_2$ under supercritical conditions (preferably using the column described hereinafter). This stage (d) serves to purify the extract.

The separating column normally to be used for the supercritical $CO_2$ gases is preferably a long pipe which is divided into 3 to 5 segments, preferably 3 segments, and in which the temperature can be changed. The product obtained from extraction (c) is introduced into the column at the base or into one of the lower segments by a pump under the same pressure as that of the column. The injected liquid moves in countercurrent to supercritical $CO_2$. The pressure inside the column must be kept constant. The required extract remains at the base while the components to be removed are stripped off by distillation.

The preferred pressure range in the column is between 110 and 180 bar, in particular between 130 and 160 bar. The temperature can vary between 34 and 80, preferably between 34 and 65, in particular between 40° and 60° C. A column with a height of 3 meters and with a diameter of 5 cm is preferably used. It is possible in this way to fractionate 2 kg of oil per hour. The fractions are always collected at the top end of the column. Unwanted and/or potentially toxic components can be removed by this countercurrent extraction.

The operating conditions which have proved most suitable for the countercurrent extraction of the extract are temperatures between 34° and 80° C., preferably from 45° to 50° C., and pressures between 120 and 180 bar, preferably 130 bar.

Figure 2:
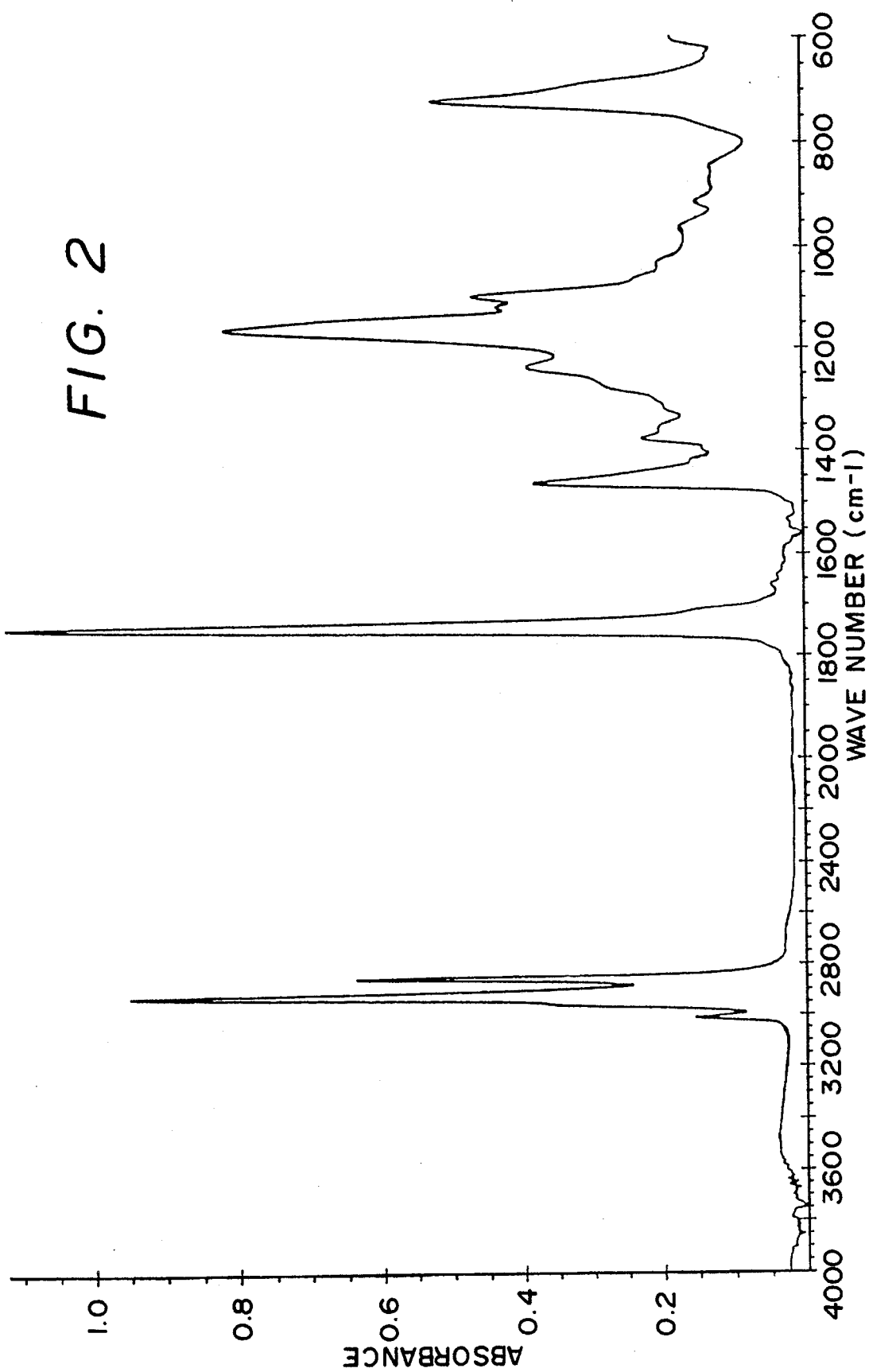
Figure 3:
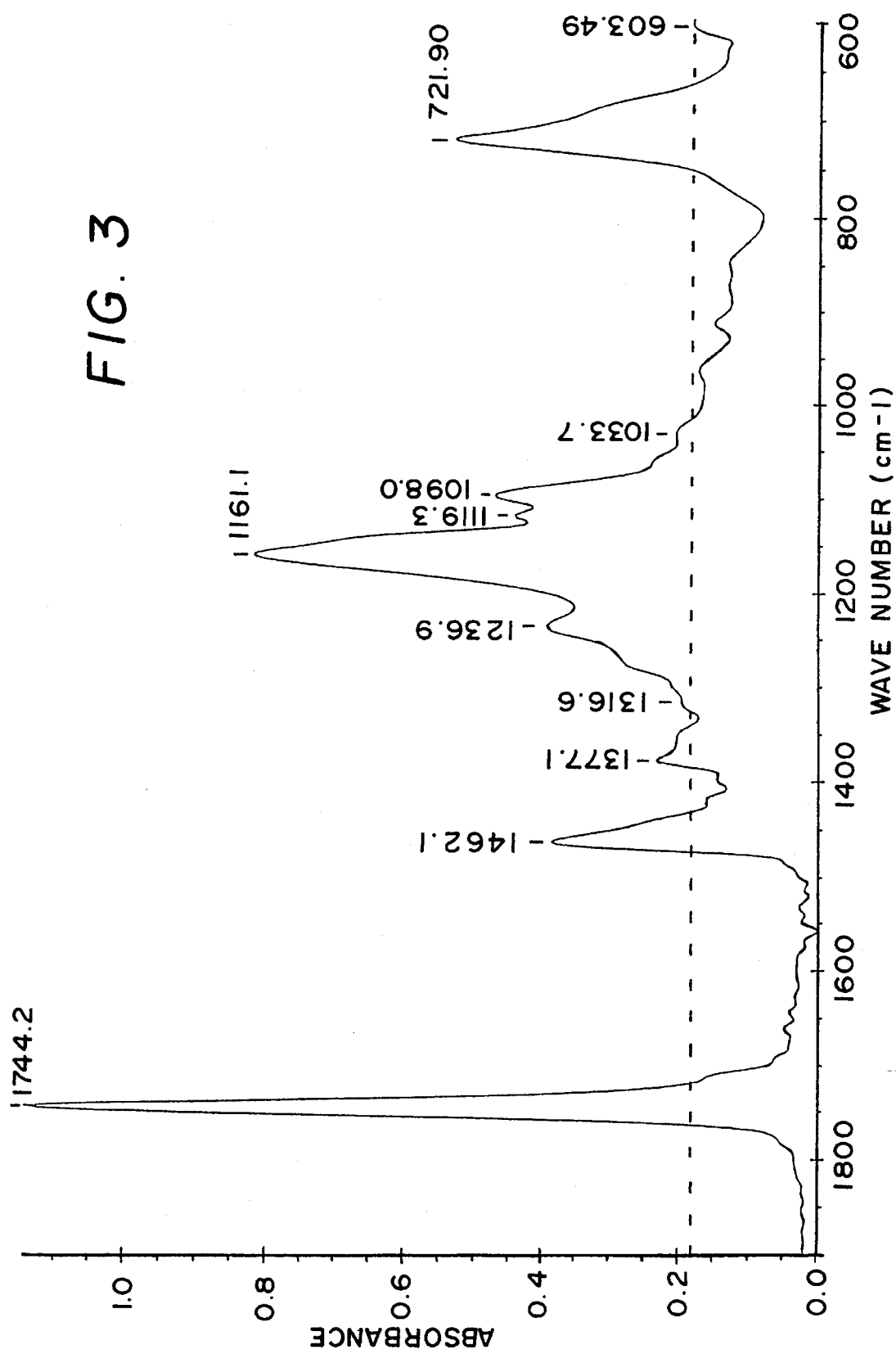
Figure 4:
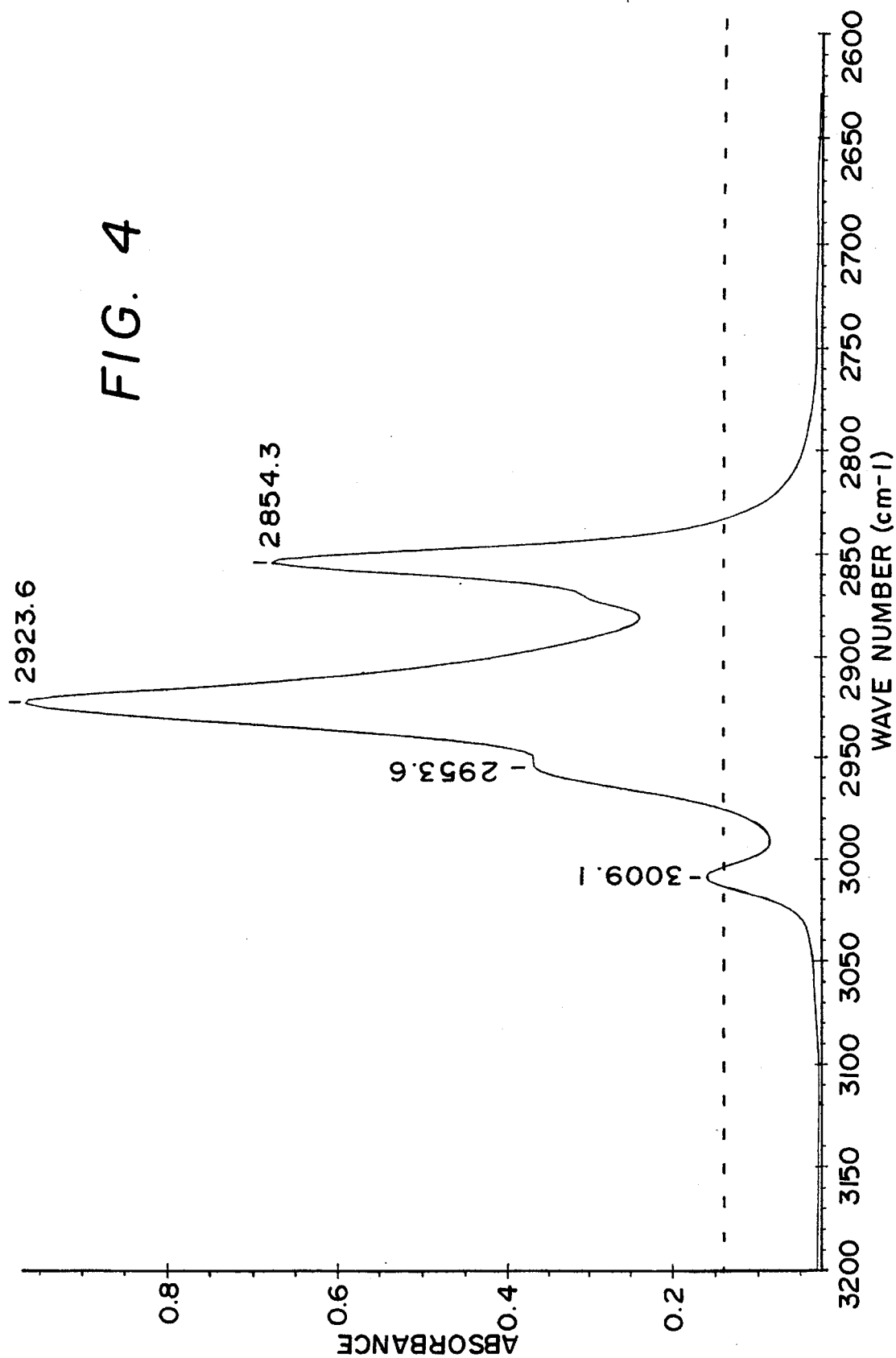

It is possible with the aid of the process according to the invention to obtain a novel extract which has about 0.2 to 0.5% sterols, 0.8 to 2% non-saponifiable residue and 82 to 94% fatty acids, and has a saponification number of 170 to 190, an iodine number of 114 to 120 and a refractive index of 1.45 to 1.48. The product preferably has an acid number of 10 to 15 and a relative density of 0.90 to 0.92 (at 25° C.). A characteristic fingerprint of a novel extract obtained by GLC-MS (gas-liquid chromatography/mass spectrometry) is shown in FIG. 1 and the FT-IR spectrum (Fourier transformed IR spectrum) is shown in FIG. 2. FIGS. 3 and 4 show particular regions of FIG. 2.

It has been found, surprisingly, that these novel extracts prepared according to the invention show in pharmacological and clinical tests a higher activity than the known extracts prepared without fractionation and used in the state of the art. Tests in vitro carried out on cultures of human prostate fibroblasts showed that the extracts according to the invention antagonize the binding of dihydrotestosterone to its specific receptors to the extent of 58% (cytosolic prostatic receptors), whereas the known complete oily extract prepared by n-hexane extraction antagonized the binding merely to the extent of 10% in a non-significant manner. This effect leads to a mechanism in which the extracts inhibit the cellular hyperplasia which represents the pathogenetic basis for benign prostate hypertrophy. The extracts also inhibit in vitro the activity of prostatic 5-alpha-reductase, i.e. the enzyme which catalyses the conversion of testosterone into dihydrotestosterone, and on this is based one of the aspects of the present invention. This effect results in an antagonism of the excessive production of this androgenic metabolite which is known to have a stimulating effect on the proliferation of the glandular tissue. The $IC_{50}$ of the extracts is about 128±25 µg/ml, whereas the known complete extract mentioned above proved to be inactive.

In vivo, in castrated rats which have just been weaned, the extracts of the Cucurbita species display a statistically significant antagonism to the effect of testosterone administered at the same time as the active substance. The extracts according to the invention show an antiprostaglandin activity which leads to an anti-inflammatory effect which is of therapeutic value for the treatment of prostatic and prostatosic disorders which are normally associated with benign prostate hypertrophy. The mechanism of action of the extract according to the invention is novel and serves as one of the aspects of the invention.

The extracts according to the invention can thus be used in particular for the treatment of pathological manifestations linked to benign prostate hypertrophy. Their range of use is therefore, in particular, the treatment of benign prostate hypertrophy and related clinical manifestations such as of prostatoses and urination disturbances.

In pharmacotoxicological respects, the extracts according to the invention show an acute toxicity in rats and mice at doses greater than 3000 mg per kg, while the doses of the extracts which elicit pharmacodynamic effects are in the range between 20 and 200 mg per kg.

It has been found that, on clinical use, the extracts according to the invention significantly reduce, in daily doses between 100 and 1000 mg, the dysuria and the frequency of urination during the day and during the night. The residual urine volume is reduced by about 70%. After treatment for six months with a dose of 400 mg per day in two divided daily administrations, the extracts lead to a statistically significant decrease of about 25% in the volume of the prostate gland.

The extracts according to the invention can be introduced into pharmaceutical formulations such as soft or hard gelatin capsules, tablets, suppositories etc. The preferred pharmaceutical formulation are soft gelatin capsules.

The medicaments according to the invention are preferably administered in a daily dose of 10 to 500 mg of extract, in particular 250 mg of extract. The administration of the daily dose preferably takes place in two divided doses, for example in the morning and evening.

The extracts according to the invention are also suitable for the treatment of skin disorders linked to androgenic metabolism, such as acne, especially juvenile acne, and seborrhoea, and are therefore also used in cosmetics. In this case, the extracts can be introduced into standard formulations such as water/oil and oil/water emulsions, detergent milk products and soaps. The concentrations recommended for adequate cosmetic efficacy are in the range between 0.1 and 2%.

The following examples illustrate the invention without restricting it.

EXAMPLE 1

Preparation of a purified lipophilic extract of *Cucurbita pepo* (Moscata variety)

The hulled seeds of *Cucurbita pepo* (Moscata variety) (50 kg) are finely milled, using a mill cooled to −5° C., and extracted with carbon dioxide under supercritical conditions at a temperature of 35° C. and under a pressure of 130 bar for 3 hours. The extractor is connected to 2 separators with the conditions in the first being 95 bar and 35° C. and in the second being 60 bar and 45° C. This leads to removal of 15 kg of straw-coloured oil which, because of its low activity, is discarded. Subsequently the plant material remaining as residue is extracted three times with 80 ml of methylene chloride each time at room temperature and under a nitrogen atmosphere. The combined methylene chloride extracts are concentrated in vacuo until the solvent is completely removed. The remaining oil (7.8 kg), which has a greenish colour, undergoes countercurrent extraction with carbon dioxide under supercritical conditions using a column with a three stages operating at different temperatures (50° C. at the head, 40° C. in the middle and 34° C. at the base) and under one pressure (of 150 bar). The separation conditions for the biologically active fraction are 50° C. and 150 bar. The distilled fraction is discarded because of its low activity, while the remaining product is collected in the column and represents the active fraction.

This oily fraction has the following characteristics: 0.38% total sterols determined by gas-liquid chromatography and expressed as β-sitosterol, 92.84% fatty acids (after saponification), 1.04% non-saponifiable residue. The oil has a saponification number of 189.5, an iodine number of 119, a refractive index of 1.4645, an acid number of 11.9 and a relative density of 0.912. The GLC profile is depicted in FIG. 1.

EXAMPLE 2

Preparation of a purified lipophilic extract from *Cucurbita pepo* (Moscata variety)

The hulled seeds of *Cucurbita pepo* (Moscata variety) (50 kg) are finely milled using a mill cooled to −5° C. and extracted with methylene chloride at a temperature of 35° C. under a nitrogen atmosphere. Four extractions with 80 l of methylene chloride each time are carried out. The collected methylene chloride extracts are treated with 0.5 kg of vegetable active charcoal and 2 kg of Celite with stirring under mild reflux to remove the turbidity. After cooling, the suspension is filtered and the solvent is removed in vacuo. This leads to separation of 22.5 kg of a greenish oil which is fractionated by countercurrent extraction in the column with carbon dioxide under supercritical conditions. The operating conditions are as follows. The column is brought under a pressure of 160 bar with a temperature gradient decreasing from the head to the base (50° C. at the head, 40° C. in the middle and 34° C. at the base). The biologically active product is fractionated at a temperature of 50° C. Use of this process results in 6.2 kg of a reddish yellow oil. The oil has the following characteristics. 0.26% total sterols and 90.45% fatty acids (after saponification). The oil has a saponification number of 184.6, an iodine number of 119, a refractive index of 1.4745, an acid number of 11.9 and a relative density of 0.914. The gas-liquid chromatogram profile essentially agrees with that previously reported in Example 1.

EXAMPLE 3

Preparation of a purified lipophilic extract from *Cucurbita pepo* (Moscata variety)

The hulled seeds of *Cucurbita* pepo (Moscata variety) (50 kg) are finely milled using a mill cooled to −5° C. and extracted with carbon dioxide under supercritical conditions at a temperature of 35° C. and under a pressure of 120 bar for 3.5 hours. This leads to removal of 15 kg of straw-coloured oil which, because of its low activity, is discarded. The remaining plant material is then extracted at 45° C. and 300 bar for 3.5 hours during which the temperature and pressure in the two connected separators are kept at 40° C. and 90 bar, and 60° C. and 50 bar, respectively, and with the recycling of the carbon dioxide being continued until completely exhausted. Use of this process results in 6.2 kg of a greenish oil. The oil is purified by countercurrent extraction under supercritical conditions in accordance with the parameters stated in Example 2. 6.1 kg of reddish oil are obtained. The oil shows the following characteristics: 0.24% total sterols and 91.54% fatty acids (after saponification). The oil has a saponification number of 182.9, an iodine number of 118.4, a refractive index of 1.4739, an acid number of 12.1 and a relative density of 0.911. The gas-liquid chromatogram profile essentially agrees with that previously reported in Example 1.

EXAMPLE 4

Preparation of soft gelatin capsules which contain 160 mg of purified Cucurbita oil extract Each of the soft gelatin capsules contains:

| Active ingredient | |
| --- | --- |
| Purified Cucurbita pepo fraction prepared according to Example 1 | 160 mg |
| Constituents of the capsule shell | |
| Gelatin | 84 mg |
| Glycerol | 32 mg |
| Ethyl p-hydroxybenzoate | 0.4 mg |
| Titanium dioxide E 171 | 0.8 mg |

What is claimed is:

1. A process for the preparation of an extract from the seeds of Cucurbita sp. comprising; (a) milling of the seeds at a temperature between −10° and +10° C. to a particle size between 0.1 and 1 mm, (b) extracting the active substances from said milled seeds with supercritical carbon dioxide at a pressure between 250 and 330 bar and a temperature between 34° and 65° C. or organic solvents at a temperature between 25° C. and the a boiling temperature of the solvent, and (c) purifying the resultant extract by fractional countercurrent extraction with supercritical carbon dioxide at a pressure between 110 and 180 bar and at a temperature between 34° and 80° C.

2. The process for the preparation of an extract according to claim 1, further comprising pre-extracting said seeds with supercritical carbon dioxide thereby removing unwanted constituents after said (a) milling of the seeds and before said (b) extracting the active substances from said milled seeds with supercritical carbon dioxide or organic solvents.

3. The process for the preparation of an extract according to claim 1, wherein said organic solvents comprise chlorinated aliphatic solvents, acetone or aliphatic alcohols.

4. The process for the preparation of an extract according to claim 1, wherein said supercritical carbon dioxide of said (b) extracting the active substances is under a pressure between 270 and 310 bar and at a temperature between 40° and 50° C.

5. The process for the preparation of an extract according to claim 2, wherein said pre-extracting supercritical carbon dioxide is under a pressure between 110 and 150 bar and at a temperature between 34° and 50° C.

6. The process for the preparation of an extract according to claim 1, wherein said (a) milling of the seeds is carried out at a temperature between −10° and +2° C.

7. An extract obtained by the process of claim 1.

8. A pharmaceutical composition comprising an anti-benign prostate hypertrophy amount of the extract of claim 7 and a pharmaceutically acceptable carrier thereof.

9. A method for treating juvenile acne and/or seborrhea comprising administering to a human being having juvenile ache and/or seborrhea an anti-juvenile acne and/or anti-seborrhea effective amount of the extract of claim 7.

10. The process of claim 1 wherein said Cucurbita sp. is selected from the group consisting of *Cucurbita pepo, Cucurbita maxima, Cucurbita moschata* and *Cucurbita pepo* var. *citrullina.*

11. An extract obtained by the process of claim 10.

12. A method for treating juvenile acne and/or seborrhea comprising administering to a human having juvenile acne and/or seborrhea an anti-juvenile acne and/or anti-seborrhea effective amount of an extract according to claim 11.

13. The method of claim 9 wherein said extract is in the form of a water/oil or oil/water emulsion, a detergent, or a soap.

14. The method of claim 13 wherein the concentration of the extract in the emulsion, detergent or soap ranges from between 0.1 and 2%.

15. The method of claim 12 wherein said extract is in the form of a water/oil or oil/water emulsion, a detergent or a soap.

16. The method of claim 15 wherein the concentration of the extract in the emulsion, detergent or soap ranges from between 0.1 and 2%.

* * * * *